US012636117B2

(12) United States Patent
Atria et al.

(10) Patent No.: US 12,636,117 B2
(45) Date of Patent: May 26, 2026

(54) SURGICAL NAVIGATION SYSTEM WITH DISTRIBUTED PATIENT REFERENCE TRACKING

(71) Applicant: nView medical Inc., Salt Lake City, UT (US)

(72) Inventors: Cristian Atria, Salt Lake City, UT (US); Luke Newmeyer, Sandy, UT (US); Lisa Last, Holladay, UT (US); Keith Nelson, Salt Lake City, UT (US)

(73) Assignee: nView medical Inc., Salt Lake City, UT (US)

( * ) Notice: Subject to any disclaimer, the term of this patent is extended or adjusted under 35 U.S.C. 154(b) by 392 days.

(21) Appl. No.: 18/168,839

(22) Filed: Feb. 14, 2023

(65) Prior Publication Data

US 2023/0310114 A1 Oct. 5, 2023

Related U.S. Application Data

(60) Provisional application No. 63/309,915, filed on Feb. 14, 2022.

(51) Int. Cl.
A61B 90/00 (2016.01)
A61B 34/20 (2016.01)

(52) U.S. Cl.
CPC .............. *A61B 90/39* (2016.02); *A61B 34/20* (2016.02); *A61B 2034/2046* (2016.02); *A61B 2090/3916* (2016.02); *A61B 2090/3983* (2016.02)

(58) Field of Classification Search
CPC . A61B 90/39; A61B 34/20; A61B 2034/2046; A61B 2090/3916; A61B 2090/3983; A61B 2034/105; A61B 2034/2048; A61B 2034/2051; A61B 2034/2055; A61B 2034/2065; A61B 2034/2068; A61B 2090/3966; A61B 90/90; A61B 90/10
See application file for complete search history.

(56) References Cited

U.S. PATENT DOCUMENTS

| | | | |
|---|---|---|---|
| 8,165,659 B2 | 4/2012 | Sheffer et al. | |
| 11,350,995 B2 | 6/2022 | Finley et al. | |
| 2002/0077543 A1 | 6/2002 | Grzeszczuk et al. | |
| 2009/0068620 A1 | 3/2009 | Knobel et al. | |
| 2010/0137707 A1 | 6/2010 | Hunter et al. | |
| 2011/0060213 A1 | 3/2011 | Mire et al. | |

(Continued)

*Primary Examiner* — Bo Joseph Peng
(74) *Attorney, Agent, or Firm* — Thorpe North & Western, LLP

(57) ABSTRACT

A non-rigid anatomy reference system can include reference markers that are rigidly attachable to separate bodies of rigid tissue connected through flexible tissue in a region of a patient forming a marker array. A tracking system can acquire movement data of the reference markers as a function of time and position. A processor can be configured to: receive the movement data, where an individual reference marker has a first number of degrees of freedom less than 6 and a second reference marker having a second number of degrees of freedom; track the marker array as a whole with a total number of degrees of freedom greater than the first and the second number; and produce an updated image of the region of the patient to maintain registration to a prior image of the region and the tracked movement of the reference markers via the function.

33 Claims, 10 Drawing Sheets

(56) References Cited

U.S. PATENT DOCUMENTS

| | | | |
|---|---|---|---|
| 2018/0042514 A1 | 2/2018 | Verard et al. | |
| 2018/0092699 A1 | 4/2018 | Finley | |
| 2018/0318035 A1* | 11/2018 | Mclachlin | A61B 90/94 |
| 2019/0070011 A1 | 3/2019 | Fanson et al. | |
| 2019/0090955 A1 | 3/2019 | Singh et al. | |
| 2019/0290365 A1 | 9/2019 | Gao | |
| 2020/0187878 A1 | 6/2020 | Edwards | |
| 2020/0188037 A1 | 6/2020 | Jacobsen et al. | |
| 2020/0237445 A1* | 7/2020 | Snyder | A61B 34/30 |
| 2021/0000380 A1 | 1/2021 | West et al. | |
| 2021/0085268 A1 | 3/2021 | Alexandroni et al. | |
| 2021/0322109 A1 | 10/2021 | Kostrzewski et al. | |
| 2022/0354580 A1 | 11/2022 | Liu et al. | |

* cited by examiner

300

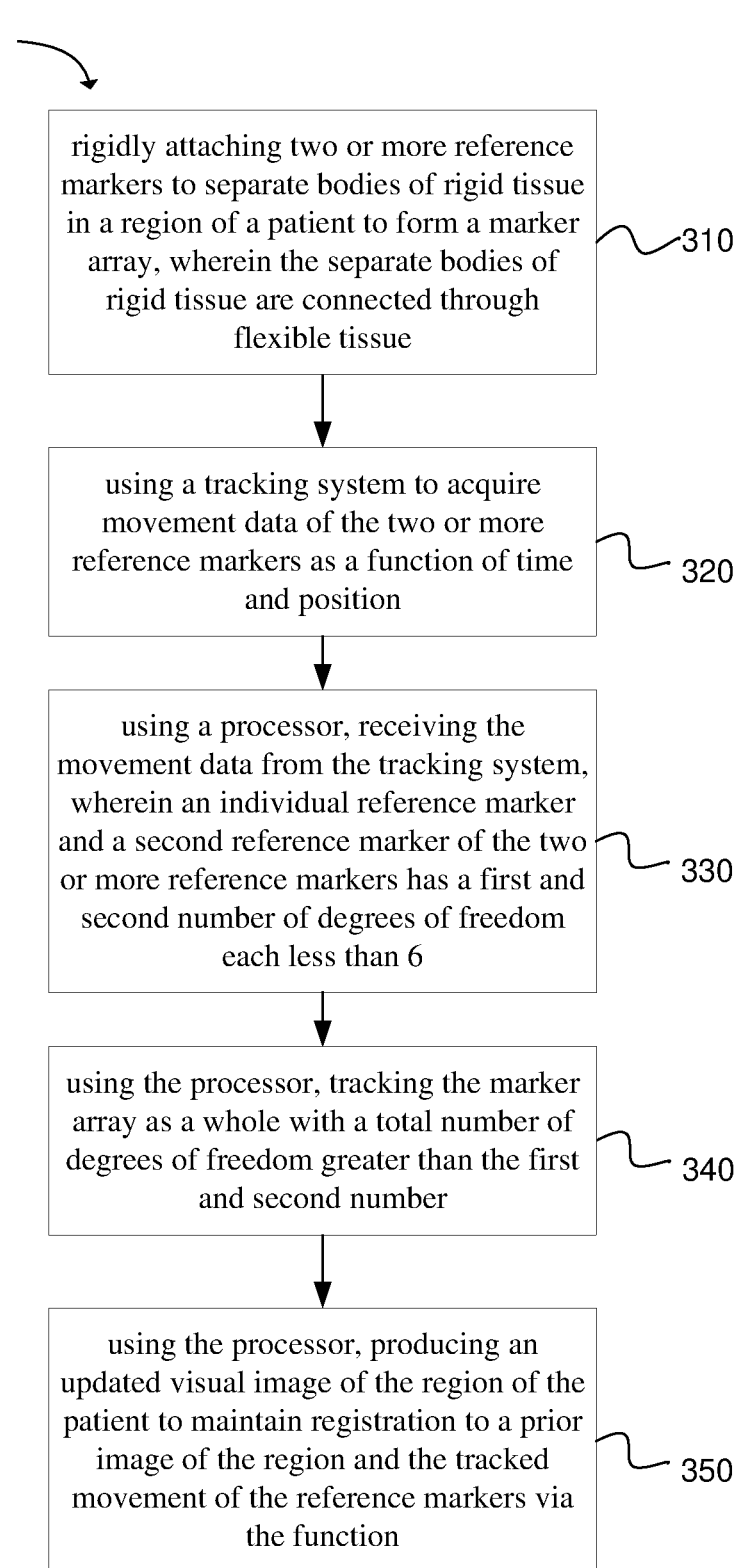

rigidly attaching two or more reference markers to separate bodies of rigid tissue in a region of a patient to form a marker array, wherein the separate bodies of rigid tissue are connected through flexible tissue ～310 using a tracking system to acquire movement data of the two or more reference markers as a function of time and position ～320 using a processor, receiving the movement data from the tracking system, wherein an individual reference marker and a second reference marker of the two or more reference markers has a first and second number of degrees of freedom each less than 6 ～330 using the processor, tracking the marker array as a whole with a total number of degrees of freedom greater than the first and second number ～340 using the processor, producing an updated visual image of the region of the patient to maintain registration to a prior image of the region and the tracked movement of the reference markers via the function ～350

FIG. 11

SURGICAL NAVIGATION SYSTEM WITH DISTRIBUTED PATIENT REFERENCE TRACKING

RELATED APPLICATION

This application claims priority to U.S. Provisional Application No. 63/309,915, filed Feb. 14, 2022, which is incorporated herein by reference.

BACKGROUND

Visual images of patient anatomy can be obtained by scanning procedures such as X-ray, computer tomography (CT) scan, Cone Beam CT (CBCT), Tomosynthesis (TOMO), and magnetic resonance imaging, (MRI). These methods can be used before a surgery to take an image of the surgical site, and may also be used periodically during surgery. However, these methods cannot be used for continuous monitoring of the patient anatomy and it is not practical to continuously repeat the scanning process throughout a surgery. Therefore, scanned images are often combined with surgical navigation systems. Surgical navigation can provide visualization of surgical instrumentation or implants as an overlay over an image of the patient anatomy, for the surgeon to view, or for consumption by robotic or intelligent surgical systems to perform, for example, surgical planning or surgical analysis. Such an overlay is accurately localized and represented with respect to the image via a registration process. Because the patient anatomy can move with respect to the tracking camera, the anatomy is also often tracked.

To track the patient anatomy, a tracked patient reference is typically used. Some patient references can be a device that is rigidly attached to bony anatomy exposed to view by a tracking camera. Such markers are often spherical. Each spherical marker can be tracked with three degrees of freedom, because the location of the marker can be tracked by one or more tracking cameras. However, the rotation of the spherical marker cannot be tracked because the rotation of a spherical marker is not discernible by the tracking camera.

To provide more degrees of freedom in tracking, some patient references have included multiple spherical markers attached to a single reference device, where the spherical markers are arranged in a non-colinear arrangement. This can allow the rotation of the reference device to be tracked and thus provide more degrees of freedom. However, such references often include additional spherical markers for redundancy in case of line of sight issues or for error reduction. This can result in bulky patient references. Other approaches have provided a single complex reference marker having elements which can provide additional degrees of freedom beyond position related to rotation. However, these devices tend to be bulky, expensive and, in some cases, can be unreliable.

SUMMARY

A non-rigid anatomy reference system can include two or more reference markers, a tracking system configured to acquire movement data of the reference markers, and at least one processor. The two or more reference markers can be rigidly attachable to separate bodies of rigid tissue in a region of a patient to form a marker array. The separate bodies of rigid tissue can be connected through flexible tissue. The tracking system can acquire movement data of the two or more reference markers as a function of time and position. The processor can be configured to receive the movement data from the tracking system. An individual reference marker of the two or more reference markers can have a first number of degrees of freedom, which is less than six. A second reference marker has a second number of degrees of freedom (e.g. also less than six). The processor can track the marker array as a whole with a total number of degrees of freedom, which is greater than the first and the second number. The processor can also produce an updated image of the region of the patient to maintain registration to a prior image of the region and the tracked movement of the reference markers via the function.

In another example of the present disclosure, a method of registering an image of non-rigid anatomy of a patient can include rigidly attaching two or more reference markers to separate bodies of rigid tissue in a region of a patient to form a marker array. The separate bodies of rigid tissue can be connected through flexible tissue. A tracking system can be used to acquire movement data of the two or more reference markers as a function of time and position. A processor can be used to receive the movement data from the tracking system, where an individual reference marker of the two or more reference markers has a first number of degrees of freedom less than six and a second reference marker has a second number of degrees of freedom. The process can also be used to track the marker array as a whole with a total number of degrees of freedom greater than the first and the second number. The processor can also be used to produce an updated image of the region of the patient to maintain registration to a prior image of the region and the tracked movement of the reference markers via the function.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 11 is a flowchart illustrating an example method of registering an image of non-rigid anatomy of a patient in accordance with an example of the present technology.

Figure 1A:
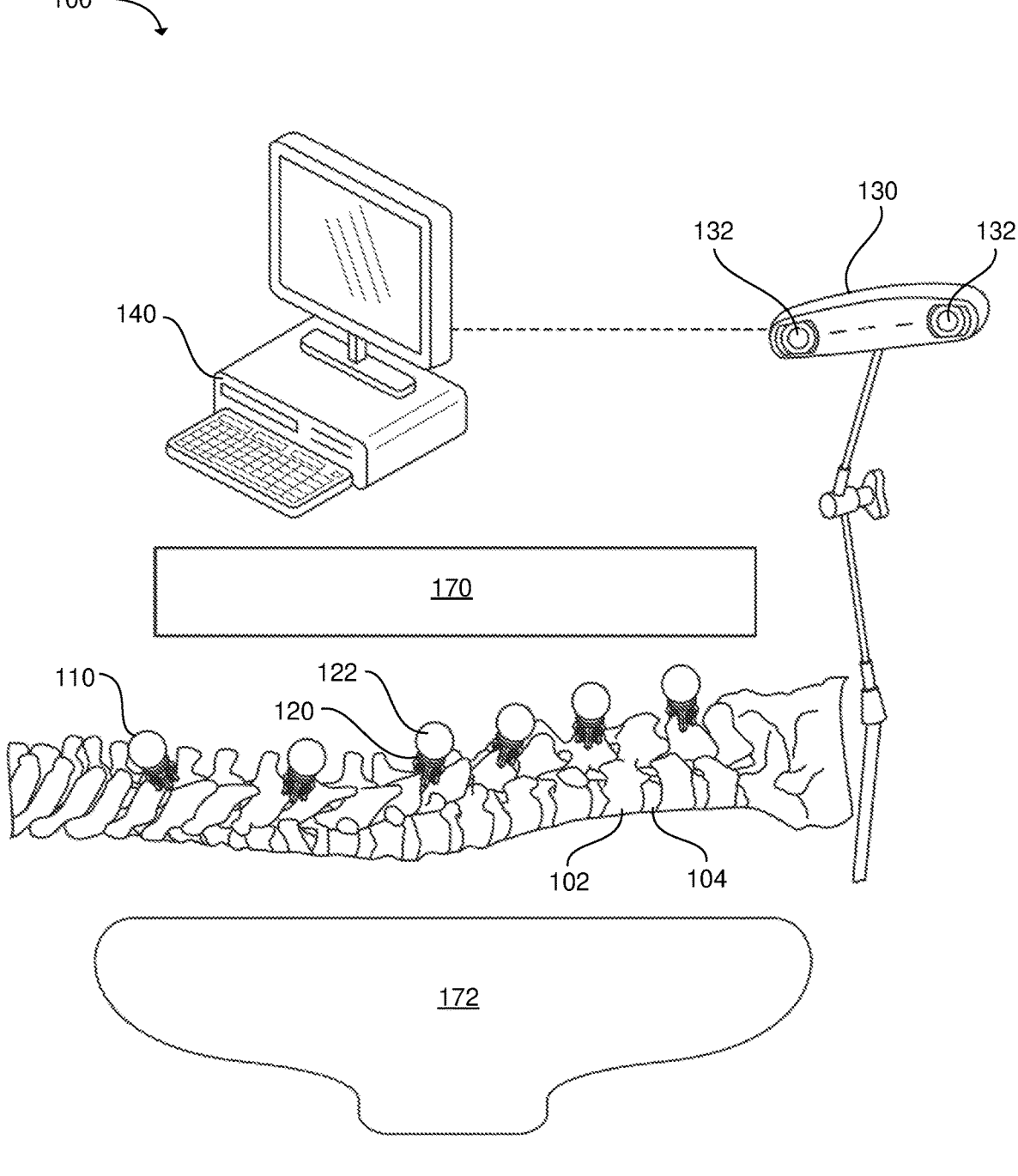
FIG. 1A is a schematic of an example non-rigid anatomy reference system in accordance with an example of the present technology.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a marker" includes reference to one or more of such features and reference to "acquiring" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein, "degrees of freedom" refers to an independent type of motion that can be tracked using the tracking systems and reference markers described herein. The degrees of freedom include the six degrees of freedom for moving a rigid object in space, which include translation motion along three axes and rotational motion about three axes. Additional degrees of freedom beyond these six can include motions such as flexing and twisting motions between bodies of rigid tissue connected by flexible tissue.

As used herein, "registration" refers to transforming different sets of data into a single unified coordinate system. In the context of the distributed reference systems described herein, the systems can maintain registration of an image of patient anatomy with movement data acquired using reference markers and a tracking system. The movement data and its registration can be represented using an updated image produced by the system. Specific methods of representing the movement data and registration are described in more detail below.

As used herein, "machine learning" refers to methods to identify and develop complex, multi-parametric, process models based on the input and outputs of a modeled process.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Present Technology

The present technology involves a distributed reference system for non-rigid anatomy. The system can include reference markers distributed on multiple separate bodies of rigid tissue, such as bones, which are connected by flexible tissue. One or more of reference markers can be tracked by a tracking system with a relatively low number of degrees of freedom. However, the system can also include a processor configured to track the array of distributed references markers as a whole with a higher number of degrees of freedom.

As mentioned above, some prior reference methods have used 6-degree-of-freedom (6-DOF) reference markers attached to the bone of interest. When rigidly attached to the bony anatomy, these markers allow the bone to be tracked with six degrees of freedom. In practice however, it is helpful to place the reference marker away from the anatomy of interest to avoid line of sight issues, reduce the risk to bump and move the reference, prevent the reference from blocking the surgical site, etc. For example, a reference marker can be attached to a different bone from the bone of interest to avoid these issues. This results in a non-rigid relationship between the anatomy of interest and the anatomy where the patient reference is attached, which can lead to inaccuracies. One particularly challenging portion of the patient anatomy is the cervical spine, where individual vertebrae move with respect to each other. However, this system can be used in any anatomical region such as, but not limited to, spinal column, hip joints, knee joints, hands, wrists, feet, ankles, shoulders, bone fragments, skull, etc.

The distributed reference systems described herein can increase accuracy when navigating such anatomy. The systems can also allow for the use of smaller and lighter reference markers compared to many prior systems. The reference markers can also be attached to separate bodies of rigid anatomy, further away from the anatomy of interest, which can avoid line of sight issues, blocking of the surgical site, and the risk of accidentally bumping the reference markers. As an example, a system as described herein can include a reference marker attached to a vertebra above the vertebra of interest, and another reference marker attached to a vertebra below the vertebra of interest, without attaching a reference marker directly to the vertebra of interest. The system can register tracked movement data with an image of the whole region, including the vertebra of interest and the other vertebrae with reference markers attached. This can allow the position of the vertebra of interest to be accurately determined and/or estimated without necessarily directly tracking the vertebra of interest. In alternative examples, a reference marker may be attached to the bone of interest and additional reference markers can be attached to other bones. In some cases, it can also be useful to attach reference markers to flexible tissue, such as the skin, cartilage, tendons, or other tissue of the patient.

The systems described herein can produce an updated image, such as an image displayed by a computer screen, which maintains registration with a prior image, such as a CBCT scan, and with movement data acquired by tracking reference markers. In various embodiments, the updated image can be produced in a variety of ways. In a simple example, the updated image can include the original, unchanged image with an overlay showing tracked locations of reference markers. In an alternative example, the updated image can be produced by rigidly shifting the original image according to movement of one or more of the reference markers. More complex methods of producing the updated image can include deforming the original image. For example, the system can utilize a deformation model, where tracked movement data of the reference markers is an input into the deformation model. A processor can use the deformation model to deform the original image and/or to deform the movement data acquired by the tracking system. The processor can then display an image including the deformed prior image and/or deformed movement data. In certain examples, the deformation model can include movement models for the specific patient anatomy, including models of movement of bones and flexible tissue. Such models can be used to estimate the locations of portions of the patient anatomy based on tracked movement data of the reference markers by accounting for geometrical movement of bone, including constraints provided by connective tissue, variations in tissue type and integrity, and surrounding tissue on such movement. These models can also be developed and augmented using machine learning.

For example, one model may be determined by segmenting bony anatomy to identify distinct bones such as vertebrae, labeling them with an index i, identifying the orientation of the vertebra (for example identifying in which direction towards which the spinous processes are pointing with algorithms such as Hough transform or singular value decomposition or the like), computing the difference in angles between adjacent vertebrae $\{Omega\_i\}$, identify the three-dimensional curve line L that connects the vertebral bodies, measure linear distances between vertebrae along L, $\{Di\}$, and assuming that the distances $\{Di\}$ can increase or decrease elastically with a coefficient Kd and the angles $\{Omega\_i\}$ can also elastically change with a coefficient Kw. The coefficients Kd and Kw can be then observed via regression or machine learning. Given a series of initial CT images of specimens (e.g. human, realistic bone models or animals), small deformations of the anatomy can be generated by applying forces similar to those expected during surgery, and a second image associated to the first is taken and analyzed to identify the second $\{Di\}$ and $\{Omega\_i\}$. The first or original $\{Di\}$ and $\{Omega\_i\}$ can be used as inputs, the new $\{Di\}$ and $\{Omega\_i\}$ after deformation along with the displacement of the tracked elements are used as the output of the deformation process given the input, and the parameter Kd and Kw are the parameters of the model that can be observed by regression for later use during surgery. Kd and Kw may be specific to specific areas (e.g. thoracic, lumbar and cervical), or more specific, down to each individual vertebra pairs.

In other examples, models may rely on Finite Element Analysis of the soft tissue and the bony tissue. Such models can be parameterized based on biological parameters such as sex, age, size, weight, biometrics or disease states. Models can be also parameterized based on the size of the reference attachment size which correlates with the distance between the bony element and the tracked marker attached to it. Location, distance and orientation of the tracked element with respect to the attachment point in the bony anatomy can be assessed by an intraoperative imaging system and further specialize the model.

In other cases, models may be as simple as warping the image assuming a parabolic or cubic deformation around the center of the image and along a single axis, similar to a flex deformation of a simple structure such as the one of a stick or rod. The flex can also be modeled with respect to specific anatomical references identified in the image and can include pivot points and axis of pivots. The model can combine simple and complex sub-models.

With the features described above, the distributed reference systems described herein can be capable of tracking patient anatomy with a greater number of degrees of freedom than an individual reference marker alone. The individual reference markers can be tracked with a number of degrees of freedom less than six. However, the system can track the patient anatomy with an overall number of degrees of freedom that is greater than six. These degrees of freedom can include translational and rotational motion of individual bodies of rigid anatomy (i.e., bones), flexing and twisting of flexible tissue between the bodies of rigid anatomy, and other movements. This tracking can be used to create a dynamic map that can be used as a manifold to dynamically warp the prior image and register a navigated instrument or implant overlay. In addition, the systems and methods allow for reduced exposure of a patient to x-rays while maintaining accuracy for a user to provide surgical intervention.

Further details about the reference markers, tracking systems, and methods of producing updated images are described below in several illustrative examples. Periodic renewed images can be acquired by an imaging device such that the prior image can be replaced with the renewed image to reset and provide a current actual representation of patient tissue and corresponding reference markers.

Figure 1B:
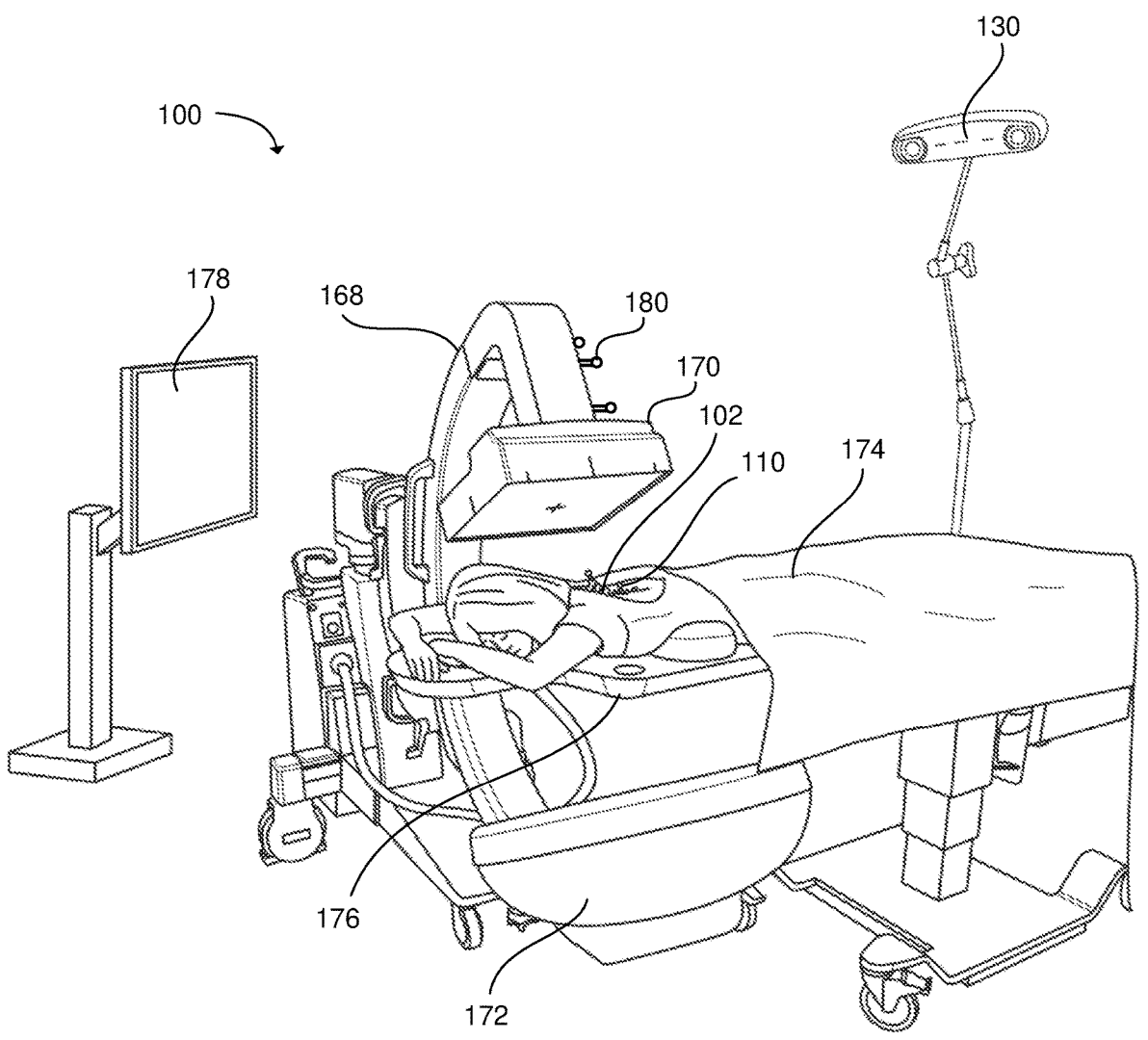
FIG. 1B is a schematic of an example non-rigid anatomy reference system in accordance with an example of the present technology including a patient bed and a 3D C-arm imaging device oriented to acquire an image.

To further describe the present technology, FIGS. 1A and 1B shows an example non-rigid anatomy reference system 100. The system includes multiple reference markers 110 that are rigidly attached to multiple vertebrae 102 of a spine. The vertebrae are separated by flexible tissue 104. In this example, the reference markers include a clip base 120 and a reflective sphere 122 attached to the clip base. The clip bases are sized and shaped to clip onto the vertebrae. The system also includes a tracking system 130. The tracking system in this example includes two infrared cameras 132 that capture infrared images of the spine and the reference markers. However, the tracking system can be any system which is capable of acquiring and reporting absolute and/or relative positions of reference markers. Other tracking systems can include, but are not limited to, optical cameras (including two or more cameras spaced apart), electromagnetic trackers, inertial systems, or computer visions cameras such as Microsoft's KINECT and the like. The tracking system is electronically connected to a processor 140 configured to receive data from the tracking system and to produce an updated image of the spine. The processor can maintain registration to a prior image of the spine and the tracked movement of the reference markers.

In the example shown above, the reference markers include reflective spheres that can be tracked by the tracking system. In particular, the spheres can reflect infrared light to make the spheres easy to capture using the infrared cameras. The spherical shape can be capable of being tracked with three degrees of freedom, namely, translational motion along three coordinate axes (i.e., up to down, side to side, and forward to backward). Although coordinate x-y-z in Cartesian system is typically used, these principles can also be applied using non-Cartesian systems such as a spherical coordinate system, cylindrical coordinate system, and the like. However, because the example sphere is symmetrical, rotation of the sphere cannot be tracked by the cameras if the sphere is non-marked. Thus, these example reference markers can be referred to as "3-DOF" markers. As shown in FIGS. 1A and 1B, multiple reference markers are attached to vertebrae of the spine. The reference markers are arranged in a non-colinear fashion. Because of this arrangement, it is possible to track the array of reference markers as a whole with more degrees of freedom. The rotation of the array can be tracked on three rotational axes (i.e., roll, pitch, and yaw). The translational movement of the array can also be tracked. Additional degrees of freedom may also be tracked, including flexing and twisting motions between the vertebrae.

In further examples of the present technology, a variety of reference markers with various degrees of freedom can be used. In many examples, at least one of the reference markers in the marker array can have a number of degrees of freedom that is less than 6. For example, the individual reference marker can have 3 degrees of freedom, 4 degrees of freedom, or 5 degrees of freedom. For example, a 5-DOF reference marker can have an elongated shape such as a cylinder. The cylinder can be trackable on three axes for translation movement, and on two rotational axes for a total of five degrees of freedom. In another example, a spherical 3-DOF marker can include an additional reference feature on the surface (i.e. a QR code, dimple, reflective spot, etc.)

which provides at least one additional degree of freedom since at least some rotational information can be extracted by comparing subsequent images of the marker.

As an example, a 4 DOF sensor can be a combination of an optically tracked sphere with 3 DOF, paired with a magnetometer or an accelerometer to provide orientation information with respect to a vertical line. As another example, a QR-code or similar coded image can be accurately tracked in two degrees of freedom by an optical camera (substantially parallel to the camera) while certain degrees of freedom such as certain orientations or depth (substantially the depth or distance to the camera) may be less accurate. An array can not only increase the degrees of freedom of the tracked object, but it can also improve the accuracy of the less accurate third, and fourth degrees of freedom from such additional features.

In the examples described herein, a statement that a reference marker "has" a certain number of degrees of freedom means that the reference markers is capable of being tracked by the tracking system with that number of degrees of freedom with a given accuracy. In some examples, all of the individual reference markers in the marker array can have less than six degrees of freedom when tracked individually. The array as a whole can have six or more degrees of freedom, meaning that the array (including all of the reference markers) can be tracked in all three translational directions, all three rotational directions, and possibly in additional degrees of freedom such as flexing movements and twisting movements. Since the system can be used on patient anatomy that may include multiple independently moveable parts, high numbers of degrees of freedom can be achieved in some examples. For example, a portion of a spine including multiple vertebrae can be tracked using the system, and the flexing and twisting motion between each individual vertebra can be tracked as independent degrees of freedom.

In some examples, one or more of the reference markers can be 3-DOF markers. In certain examples, all of the reference markers in the array can be 3-DOF markers. For example, the 3-DOF markers can include a single sphere, and a single marker can be attached to a single body of rigid anatomy such as a bone. Therefore, the bones that have a 3-DOF reference marker attached can be tracked individually with three degrees of freedom. However, the marker array as a whole can be tracked with a higher number of degrees of freedom. Therefore, the system can also track the region of the patient anatomy, including the bones having markers attached, with a higher number of degrees of freedom. In one example, two 4-DOF markers (e.g. spheres with a magnetometer) can be provided to collectively achieve more than six degrees of freedom. In certain examples, the marker array can include two or more 3-DOF markers arranged in a non-colinear arrangement, and in some cases three or more. This can allow the marker array to be tracked with at least five degrees of freedom, and in turn the patient anatomy can be tracked with at least six degrees of freedom.

Other combinations of reference markers in various arrangements can also allow the array to be tracked with at least six degrees of freedom. For example, the marker array can include two reference markers that are each individually trackable with five degrees of freedom. When combined in a marker array, the marker array as a whole can be tracked with at least six degrees of freedom.

The reference markers can include an imageable portion that can be imaged by the tracking system and/or by a scanning system such as X-ray, CT scanning, MRI, etc. In some examples, the imageable portion can be reflective like the reflective spheres in the examples above. The imageable portion can be reflective to visible light, infrared light, or both. In various examples, the imageable portion can be made from a reflective material or coated with a reflective coating. such as NDI Passive Sphere™. In other examples, the imageable portion can actively emit light. For example, a visible light emitting diode (LED) or infrared LED can be included in the imageable portion. In further examples, the imageable portion can be radiopaque. This can allow the reference marker to be imaged by X-ray, CT scanning, MRI, or other scanning technology during acquisition of a true accurate image. In certain examples, the imageable portion can have a combination of these characteristics, such as being made from a material that is both reflective and radiopaque.

In one example, an initial image of the patient anatomy can be taken by X-ray or CT scan using the image device 168. In this case, the imaging device is a 3D C-arm device capable of providing CBCT imaging or TOMO imaging including an X-ray source 170 and detector array 172. This image can be taken when the reference markers 110 have already been attached to the patient anatomy and becomes the prior image as a basis for later updates as described herein. As particularly illustrated in FIG. 1B, the non-rigid anatomy reference system 100 includes the tracking system 130 which reports to a processor. A patient 174 can be oriented on a corresponding support bed 176. The reference markers 110 can be distributed and rigidly attached to vertebrae 102 of the spine (although other anatomical positions can be marked, tracked and imaged in the same manner). During surgery a user can periodically acquire a renewed image in order to reset the prior image to a current actual image of the patient and reference markers. The renewed image and subsequent updated images can be displayed on a screen 178.

As can be appreciated, the approach described herein provides updated images which are merely guides and/or extrapolations of a true location of tissue relative to the reference markers in order to reduce exposure of a patient to excessive x-rays. As such, although providing valuable information, these updated images can eventually become excessively unreliable and non-representative of actual tissue locations. Therefore, periodic renewed images can be acquired and used as the prior image in order to resynchronize the system with actual current image information. These periodic updates can be triggered manually by the user, automatically at predetermined intervals, or when suggested by an automatic system (for example based on a confidence metric that tests for rigid motion based on multiple tracked markers).

The reference markers can include radiopaque imageable portions so that the reference markers show up clearly on the initial scan image. The imageable portions can also be reflective, which can make them clearly visible to the tracking system. In certain examples, the tracking system can include an infrared camera and an infrared light source. The reflective imageable portions of the reference markers can reflect the infrared light so that the reference markers are easily imageable by the tracking system. The tracking system can then be used to acquire and transmit changes in position of the reference markers during a surgery to the processor.

The shape of the imageable portion of the reference markers can affect the number of degrees of freedom of the reference markers. An imageable portion with a spherical shape can typically be tracked with three degrees of freedom, because the spherical shape does not visibly show any rotational movement. In other examples, the imageable portion can be shaped as a cylinder, a cube, or other shape. These shapes can provide additional degrees of freedom if they display rotational movement around one or more axes, which can be visible to the tracking system. Additional degrees of freedom can be added by including spots or portions which are differentiably reflective from other parts of the surface, flat areas, dimpled locations, QR codes or other images printed on a surface, and the like. These references markers can also be formed of a material and shape to provide a lightweight marker which has negligible effect in causing movement of the bone or tissue to which it is attached. As a general guideline, each reference marker can have a weight which is less than about 8 grams, in some cases less than 5 g, in other cases less than 3 grams, and in yet other cases less than 2 grams. Similarly, the size of the reference markers can be less than 7 cm, and in some cases less than 5 cm in height, with a width less than 2.5 cm, and in some cases less than 1.5 cm in width.

It can be useful to have the imageable portion of the reference marker held at a distance away from the patient anatomy. This can make the imageable portion easier to view by the tracking system, reduce line of sight obstructions during surgery, and keep the imageable portions farther away from the surgical site, surgical instruments, and hands of the surgeon. In some examples, the reference marker can include a base that includes a spacer. The spacer can be adjacent to the imageable portion. The spacer can hold the imageable portion away from the anatomy to which the reference marker is attached. In various examples, the spacer can space the imageable portion away from the rigid tissue of the patient by about 5 mm to about 5 cm, or about 5 mm to about 3 cm, or about 5 mm to about 2 cm, or about 5 mm to about 1 cm, or about 1 cm to about 5 cm, or about 1 cm to about 3 cm, or about 2 cm to about 5 cm. The width or diameter of the spacer can be from about 2 mm to about 2 cm, or from about 3 mm to about 1.5 cm, or from about 4 mm to about 1 cm, in some examples.

The reference marker can attach to the anatomy of the patient in various ways. In some examples, the reference marker can attach to the patient anatomy by a clip, an adhesive, a screw, a pin, a clamp, or other attachment method. In certain examples, the reference marker can include a clip base with a clip configured to be manually clipped onto rigid tissue and manually removeable from the rigid tissue.

Optionally, additional device reference markers 180 can be oriented on a surface of the imaging device 168 facing the tracking system 130. In this manner, the tracking system 130 can capture and relay information regarding a position of the imaging device 168 relative to patient reference markers 110. This can allow for additional reference points in alignment of an acquired image using the imaging device 168 with subsequent tracking of reference markers.

Figure 2:
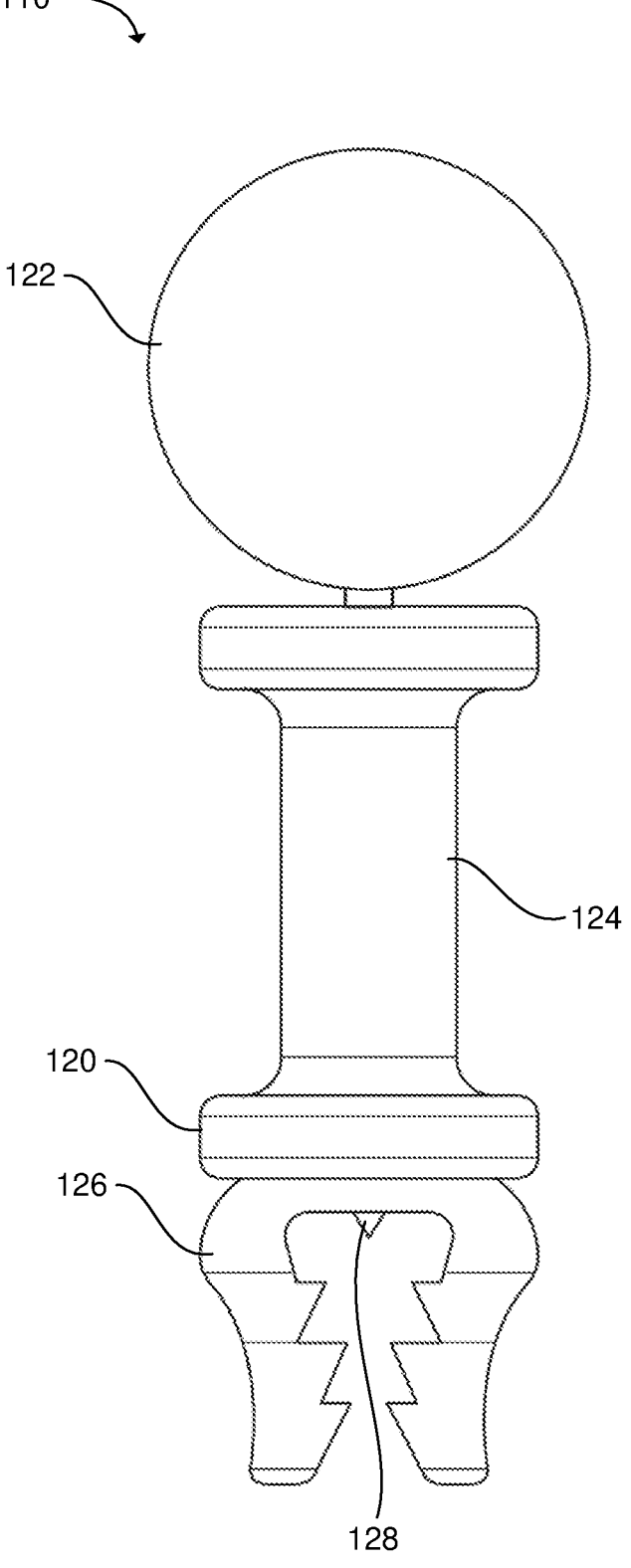
FIG. 2 is a side view of an example reference marker in accordance with an example of the present technology.
Figure 3:
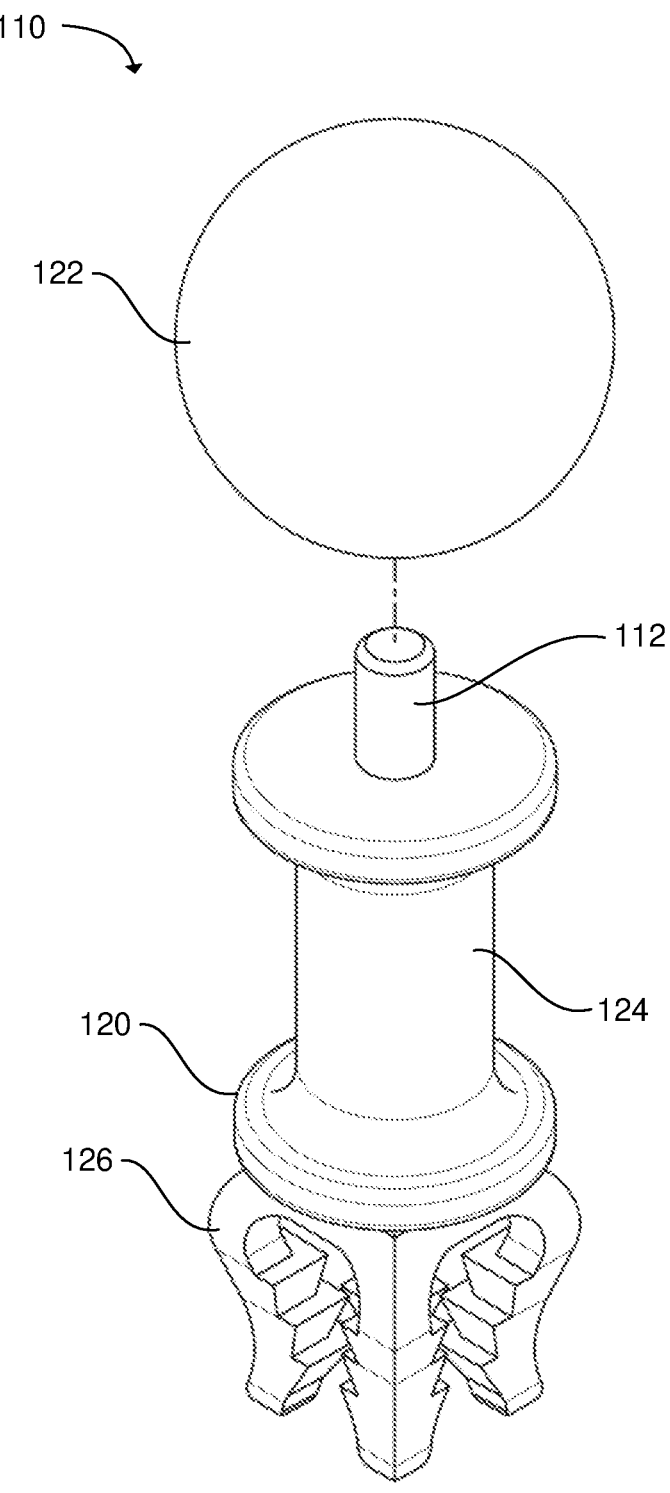
FIG. 3 is a perspective view of an example reference marker in accordance with an example of the present technology.

FIG. 2 shows a side view of an example reference marker 110. This reference marker includes a clip base 120 with a reflective sphere 122 attached to the clip base. The reflective sphere is the imageable portion in this example. The clip base includes a toothed clip 126 that has multiple legs and teeth on inner surfaces of the legs. These clip legs are configured to fit over a vertebra in a spine of a patient. The teeth on the inner surfaces can grab onto the bone and prevent the clip from sliding after it has been attached to the bone. However, the clip can be manually pulled off the bone by tugging without sufficient force to cause undue damage to the bone. This example also includes a downwardly pointing spike 128 positioned between the legs of the clip. This spike can contact the bone when the clip is fully seated, and the spike can further help prevent movement of the clip with respect to the bone. The reference marker also includes a spacer 124 between the clip and the reflective sphere. The spacer in this example is shaped as an ergonomic grip. The ergonomic grip is sized and shaped to admit a finger or thumb of a user, so that a user can grasp the reference marker with a sturdy grip between the finger and thumb when placing or removing the reference marker, protecting the marker for example from soiling the marker with blood or other pollutants that may degrade its performance FIG. 3 shows a perspective view of a similar example reference marker 110. This reference marker also has a clip base 120 with a toothed clip 126 and a spacer 124 shaped as an ergonomic grip. The downward pointing spike is not visible from this angle. In this figure, the reflective sphere 122 is a separate part that can be attached to the clip base by placing the reflective sphere onto a peg 112 at the top of the spacer. In other examples, the imageable portion of the reference marker can be a sphere or other shape that is integrated into the clip base. In certain examples, a reflective and/or radiopaque coating can be applied to the imageable portion without being applied to the clip base.

The clip can be sized to fit onto a particular body of rigid tissue such as a particular bone. The size of bones, such as vertebrae, can vary widely from patient to patient and different vertebrae also vary in size within the same patient spine. In certain examples, the clip can be sized to fit onto a spinous process. In some examples, multiple reference markers having differently sized clips can be used on a single patient. The clip can have a space between the legs of the clip that is from about 1 mm to about 2 cm when the clip is not attached to a bone. Other sizes for the space between the legs of the clip can be from about 2 mm to about 1.5 cm, or from about 3 mm to about 1 cm, or from about 4 mm to about 8 mm, or from about 2 mm to about 8 mm, or from about 1 mm to about 5 mm. Additionally, the legs of the clip can be somewhat flexible so that the legs can flex outward to admit a bone that is slightly larger than the space between the clip legs.

It certain examples, the systems described herein can include a kit comprising multiple reference markers having differently sized clips. This can allow a user to select reference markers with appropriately sized clips to attach to specific bones of a particular patient. For example, a kit can include a small clip, a medium clip, and a large clip. In another example, the kit can include two or three or more reference markers with each of the clip sizes. The number of reference markers used in a particular surgery can depend on the number of bones being tracked and preference of the user. The kit can include sufficient reference markers for use in a particular surgery. In some examples the kit can have from 2 to 10 reference markers, or from 2 to 8 reference markers, or from 2 to 6 reference markers, or from 2 to 4 reference markers.

The reference markers can be made using any suitable manufacturing process from any suitable material. In some cases, the reference markers can be made from plastic by an additive manufacturing process, injection molding, machining, or other manufacturing process. Additive manufacturing processes that can be used include fused deposition modelling, stereolithography, multi-jet fusion, selective laser sintering, binder jetting, and others. Some examples of materials that can be used to make the reference markers include biocompatible materials, polyamide, polylactic acid, acrylonitrile butadiene styrene, thermoplastic polyurethane, polycarbonate, photocurable resin, and others.

One or more of the reference markers can be a composite reference marker. As used herein, "composite reference marker" refers to a reference marker that has multiple trackable portions attached to a common support. For example, a composite reference marker may have multiple reflective spheres attached to a common support. The multiple trackable portions can be arranged in a non-colinear arrangement, which can provide additional degrees of freedom for the composite reference marker. The common support can be attachable to a body of rigid tissue. In certain examples, the common support can include a single clip such as the clips described above. To differentiate from composite reference markers, the term "independent reference marker" can refer to a reference marker that has a single trackable portion. As described herein, the tracker can be rendered trackable by using an optical imaging system, an embedded electromagnetic coil which is detected using a corresponding coil or receiver, or other tracking options, In certain examples, the system can include at least one independent reference marker and at least one composite reference marker.

Figure 4:
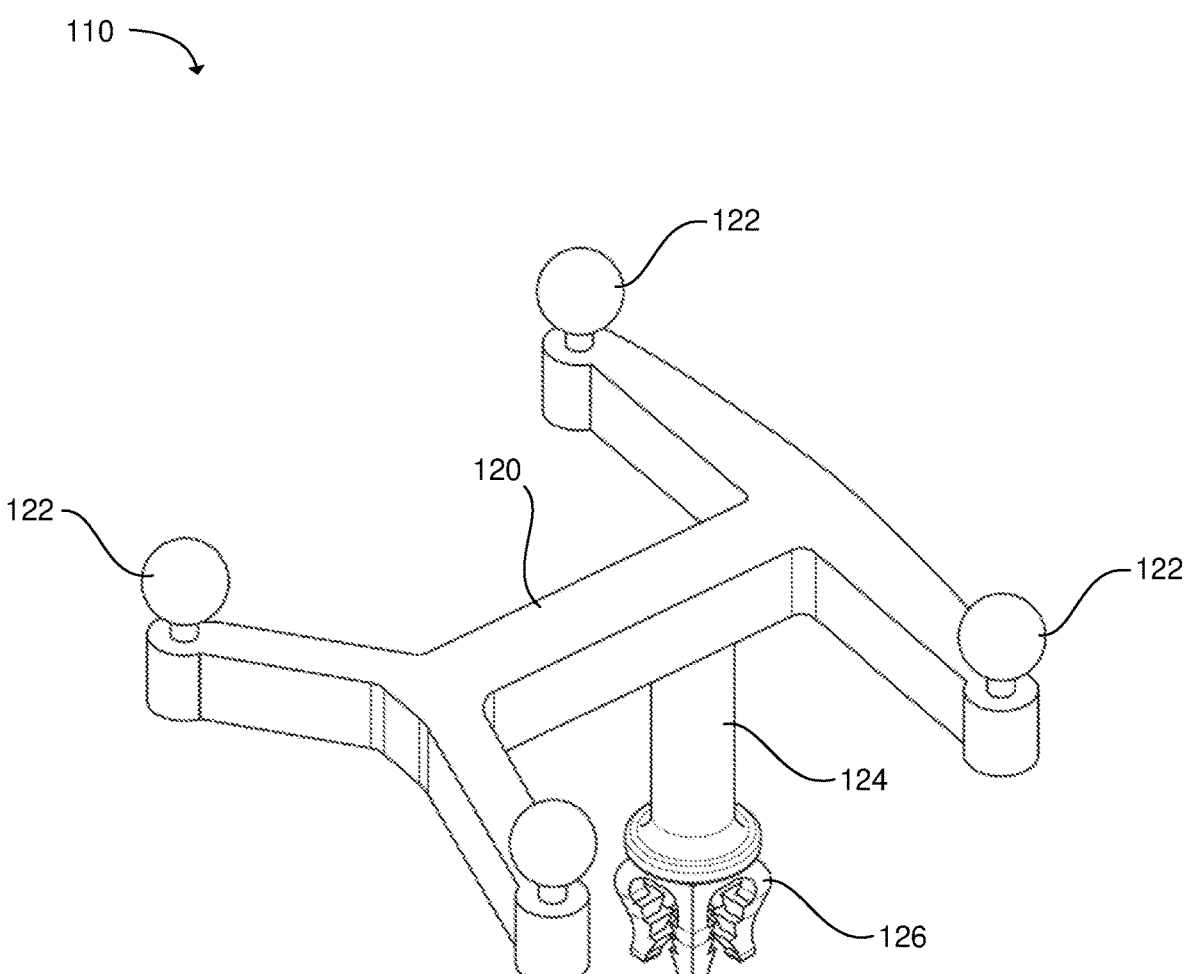
FIG. 4 is a perspective view of an example composite reference marker in accordance with an example of the present technology.

FIG. 4 shows a perspective view of an example composite reference marker 110. This example includes a common base 120 that has four reflective spheres 122 attached. The reflective spheres are arranged in a non-colinear arrangement. This can allow the composite reference marker to be tracked with more degrees of freedom than a reference marker with a single reflective sphere. This example also includes a spacer 124 and a clip 126, which are parts of the common support.

The systems described herein can also include surgical instruments that have reference markers that allow the surgical instruments to be tracked by the tracking system. The reference marker of a surgical instrument can be referred to as an instrument marker. In some examples, an instrument marker can be a composite-type marker, with multiple imageable portions such as multiple reflective spheres. This can increase the number of degrees of freedom with which the surgical instrument can be tracked. In certain examples, the surgical instrument can be tracked with at least 6 degrees of freedom. The instrument marker can be integrated in the surgical instrument in some examples, or in other examples the instrument marker can be a separate attachment that attached onto the surgical instrument.

Figure 5:
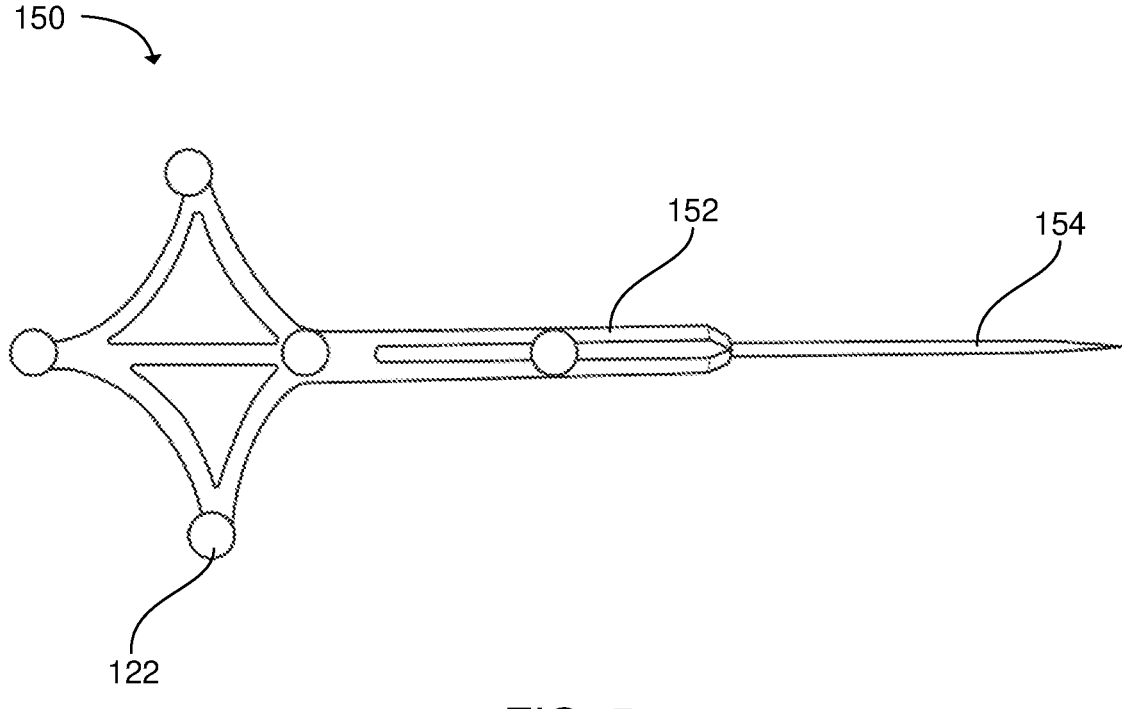
FIG. 5 is a top plan view of an example tracked instrument in accordance with an example of the present technology.
Figure 6:
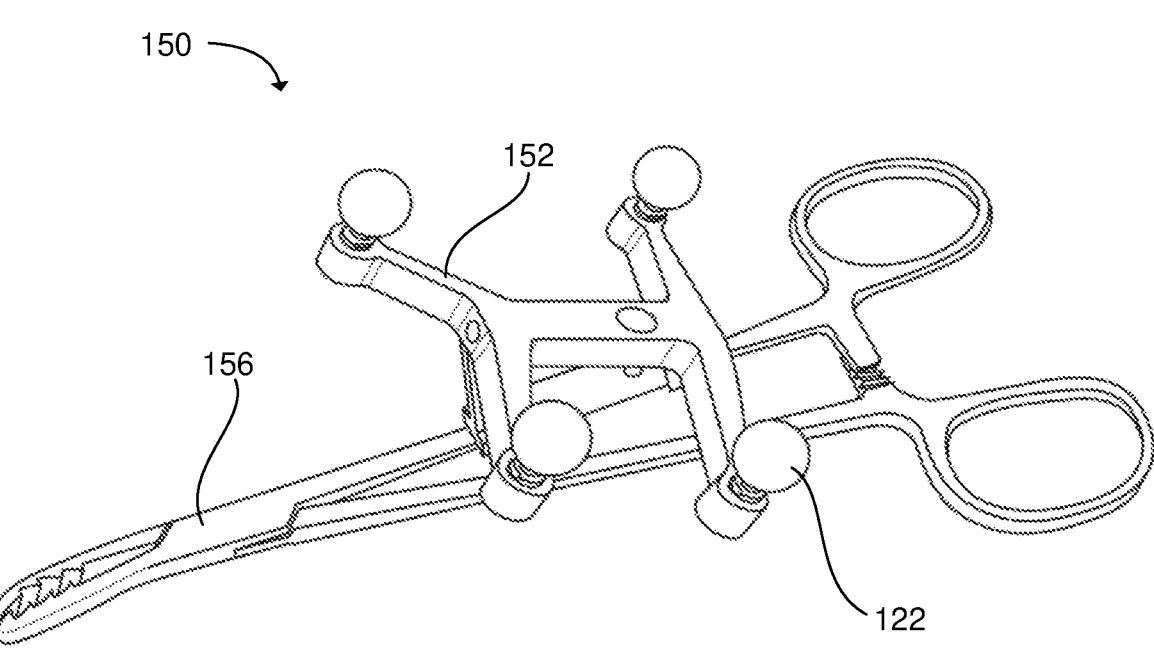
FIG. 6 is a perspective view of another example tracked instrument that can be also used as a patient reference in accordance with an example of the present technology.

FIG. 5 shows an example surgical instrument 150 that includes an instrument marker 152. The instrument marker includes multiple reflective spheres 122 arranged in a non-colinear arrangement. This example instrument also includes a probe needle 154 at the tip of the instrument. FIG. 6 shows another example surgical instrument 150. This surgical instrument includes a clamp 156 with an instrument marker 152 attached to the clamp. This instrument marker also includes multiple reflective spheres 122 in a non-colinear arrangement. Surgical instruments with instrument markers can be tracked by the tracking system along with reference markers attached to the patient anatomy. The tracking system can acquire movement data for these reference markers to be used in generating an image to display to a user. The tracking of the instruments and the patient anatomy can provide a user with more information about the relative positions of the surgical instruments and the patient anatomy.

Implants are a particular type of surgical instrument that is intended to be implanted in the patient. In some examples, the systems can also include implants with reference markers to track movement of the implants. A reference marker of an implant can be referred to as an "implant marker." Similar to the other reference markers described above, the implant marker can be an independent marker with a single imageable portion, or a composite marker with multiple imageable portions. In certain examples, the implant marker can be an integral part of the implant that is intended to remain with the implant in the patient body. In other examples, the implant marker can be detachable. For example, after an implant is in place, the implant marker can be detached from the implant. Methods of detaching the implant marker can include cutting, unscrewing, unclipping, unpinning, or other methods.

The tracking system used in the systems described herein can include an imaging device such as a visible light camera or an infrared camera. In further examples, multiple cameras can be used. For example, a pair of cameras can be used to provide stereoscopic vision. Alternatively, multiple cameras can observe the reference markers from different angles, such as an overhead camera and a side camera.

In other examples, the tracking system can utilize electromagnetic tracking. In some such tracking systems, an electromagnetic field can be generated in the space encompassing the patient anatomy of interest. The electromagnetic field can have a varying intensity and direction in space, and the geometry of the field can be known. When such a tracking system is used, the reference markers can include an electromagnetic sensor that can sense the electromagnetic field. Information provided by the sensor can be compared to the known geometry of the electromagnetic field to determine the location and/or orientation of the sensor. Various types of electromagnetic tracked elements can be sensors including coils, concentric coils, concentric coils arranged around three orthogonal axis, wired induction sensors and the like, or localizable emitters such as active coils, magnetic strips, etc Typically, in electromagnetic tracking, a single coil can be tracked with up to 5-DOF.

The tracking system can be connected to at least one processor. The tracking system can acquire movement data of the reference markers as a function of time and position, and the processor can receive this movement data and produce an updated image based on the movement data. In particular, the processor can maintain registration between a prior image of the patient anatomy and the tracked movement of the reference markers. This can provide a user, such as a surgeon, with information about how the patient anatomy has moved compared to the prior image. Several methods can be used by the processor to maintain registration of the image with the movement data and display information to the user, as detailed below. The prior image can be an image recorded using X-ray, CT scan, CBCT, TOMO, MRI, or other scanning methods in some examples. In some cases, the prior image can be recorded using CBCT or TOMO.

In the case of a user which is a physician, surgeon or other human the updated image can be an updated visual image which is displayed to a screen. However, in cases of an automated robotic surgical system, the updated image can be entirely electronically utilized such that a display screen is not necessary.

In some examples, the processor can produce an updated image by registering the prior image to movement data through rigid registration. As used herein, "rigid registration" can refer to rigidly moving the prior image or the tracked position of the reference markers without changing the proportions of the prior image or the tracked locations of the reference marker array as a whole. Rigid movement can include translation and/or rotation of the prior image. Although tissue and bone may have moved and be arranged differently than shown the original image, such rigid registration can still provide significant guidance to a user to improve orientation of a surgical tool with respect to tissue. In one example, the processor can rigidly move the prior image in a direction of movement of at least one of the reference markers. In a particular example, the prior image can be rigidly moved in the same direction of movement by the same distance as the movement of one of the reference makers. Thus, the updated image can be aligned precisely with the new location of the reference marker that has moved. In some cases, more than one of the reference markers may move in the same direction and the same distance. In these cases, the image can be rigidly moved to align with all of the reference markers that moved in the same direction and the same distance. It is noted that when this method is used, if one or more of the reference markers did not move the same direction and/or distance, then the updated image will likely be inaccurate in the vicinity of these markers. In certain examples, the processor can display information the user indicating which reference marker has been used to rigidly align the updated image. This can tell the user that the updated image is likely to be most accurate in the vicinity of that reference marker. Any reference markers which do not move with the others can be disregarded entirely from a calculation of the direction of movement for the image. Alternatively, the direction of movement can be calculated as an equal average of the movement of all of the reference markers. In yet another alternative, the direction of movement can be calculated by a weighted average where any reference markers which move differently from a majority of other markers are included at a lesser weight. Furthermore, the prior image can be enlarged and/or compressed as an additional degree of freedom to account for imperfections of difference in scale between the tracking system of the imaging system. For example, MRI and TOMO systems may deform the acquired image such that some local or global scaling (i.e. enlargement and/or compression) of the acquired image can be performed to improve accuracy.

Rigidly moving the reference marker locations can refer to altering the movement data received from the tracking system. The movement data recorded by the tracking system can include an image of the locations of the reference markers. In some cases, this can be a literal image recorded by a visible light camera or an infrared camera, or multiple images recorded by multiple cameras. If an electromagnetic tracking system is used, the "image" of the reference marker locations can be generated using the locations of the reference markers detected using the tracking system. In some cases, the data recorded by the tracking system can be referred to as the camera space, relative to the tracking system (typically a camera system, but can be an emitter space of an electromagnetic system). This is differentiated from the image space, which refers to the space where the prior image is taken relative to the imaging system. In various examples, either the image space or the camera space can be modified when registering the prior image and the movement data. In the present example, rigidly moving the camera space can involve moving the tracked locations of all the reference markers. In certain examples, the prior image can be maintained without moving the prior image, and the tracked locations of the reference markers can be moved to align with the prior image. As before, if one of the reference marker locations is used to align the camera space with the image space, the updated image is likely to be most accurate in the vicinity of that particular reference marker. If the locations of other reference markers do not align with their locations in the prior image after this rigid shift, then the updated image is likely to be less accurate in the vicinity of those other reference markers. In these cases, any one or more reference markers which are included in the alignment calculation can be highlighted for the user so that accuracy of the shifted image adjacent those markers can be judged by the user as more accurate than those which were not included. Notably, the user can be a human operator (e.g. physician or surgeon). However, in some cases the user can be an automated surgical system which uses this anatomy reference system to register the robotic space which may have an independent tracking system. Regardless, the updated images and tracking data can be used as input to such an automated surgical system.

In another example, the prior image can be rigidly moved by an average of movements of the reference markers. For example, multiple reference markers may move different distances and/or in different directions. The average distance and average direction can be determined by the processor and then the processor can update the image by rigidly moving the prior image by the average distance in the average direction. For example, the average movement can be assessed as a translation and rotations in 3D space via a point-cloud registration method. This method can result in better overall accuracy for aligning the image with the reference markers. However, if a reference marker is an outlier that moves a drastically different distance or direction that the other reference markers, then the image is likely to be inaccurate in the vicinity of the outlier. Including the outlier in the average also reduces the accuracy of the image in the vicinity of the other, non-outlying reference markers. Accordingly, it may be useful to exclude some reference markers from the average. In certain examples, the processor can determine a confidence level for each reference marker. The confidence levels can be compared against a predetermined confidence level threshold. Any reference markers that fall outside of this predetermined confidence level can be excluded from the average. In further examples, the average can be a weighted average. Different reference markers can be weighted differently in the average depend on various factors. In some examples, the confidence level of the reference markers can be a parameter in weighting the contribution of the reference markers to the average. The confidence level may be the residual error of a point-cloud registration method, or a metric derived from the residual error. One criteria used to assess whether a residual is acceptable or not is when it is more likely to be explained by the reference detaching from the anatomy than by the model being inaccurate. In other words, when the model was observed with realistic deformations, residuals can be assessed and explained by model imperfections and bound to values seen during the model observation process; When the system is tested for misuse such as detachment of the references, or bumping of the references, higher residuals will be observed. A threshold may be a value that is smaller than these observed residuals during misuse, but higher than the residuals seen under controlled use without misuse.

In other examples, a navigated instrument such as the surgical instruments described above can be tracked by the tracking system. The reference markers that are nearer to the navigated tool may be tracked more accurately than more distant reference markers. Therefore, the proximity of the reference markers to the navigated instrument can also be a parameter used in weighting the contributions of the reference markers to the average.

Rigid movement of the image space or camera space can include translational movement, such as shifting the image or camera space up, down, left, or right. For example, the updated image can be produced by shifting the prior image in any of these directions based on the movement data of the reference markers. Rigid movement can also include rotation. For example, the prior image can be rotated in a clockwise or counterclockwise direction based on the movement data of the reference markers around a certain axis, or subsequent rotations around different axes. In certain examples, both translational and rotational rigid movement can be utilized.

Figure 7:
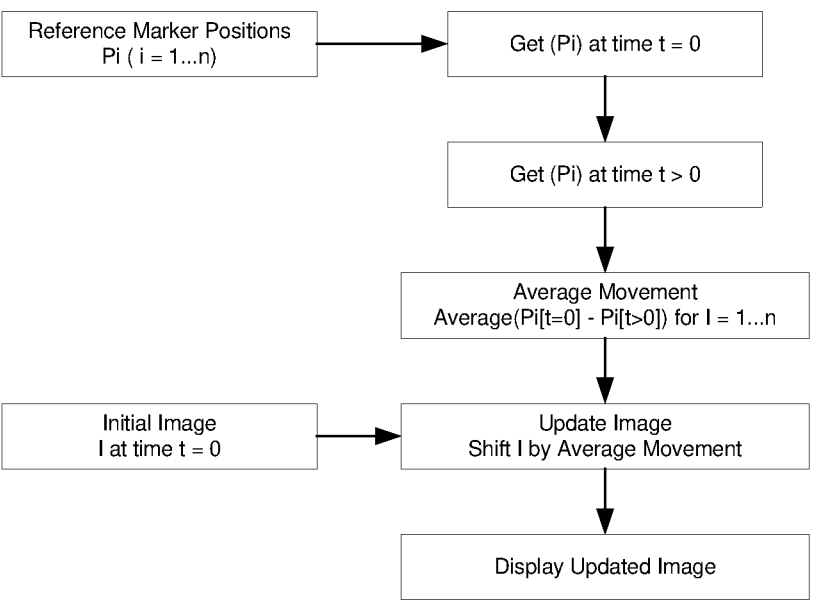
FIG. 7 is a flowchart illustrating an example algorithm in accordance with an example of the present technology.

FIG. 7 is a flowchart illustrating an example algorithm for producing an updated image by rigid movement. In this example, the positions of individual reference markers in the system are represented by $P_i$. For 3-DOF reference markers, the positions can include an xi, y, and z, value. The positions of the reference markers are input as parameters into the algorithm. The initial positions are recorded at the beginning (t=0). Then, the positions are found at later times (t>0) using the tracking system. This algorithm shifts the image by an average of the movements of the reference markers. Thus, the average difference between the initial positions and the updated positions is found. The initial image taken at time t=0 is then input as a parameter, and this image is updated by shifting the image by the average of the movements of the reference markers. The updated image is then displayed to a user.

Producing the updated image can also involve adding movement indicia to the image. Movement indicia can be any information about movement of the reference markers, which can be displayed to a user in the updated image. In some examples, movement indicia can be overlayed on the prior image. Examples of movement indicia that may be useful include indicators showing the position of reference markers as tracked by the tracking system in real time. In one such example, the updated image can include the original prior image, without any movement or change to the prior image, plus an overlay showing the currently tracked positions of the reference markers. The reference markers can also be visible in the original prior image. Therefore, a user can visually see whether the reference markers have remained at their original locations or moved to new locations. The user can also deduce that the rest of the image is likely to be more accurate near reference markers that have remained close to their original locations, and less accurate near reference markers that have moved farther from their original locations. Another example of movement indicia can include movement vectors, showing movement direction and/or distance for reference markers that have moved during tracking.

Figure 8:
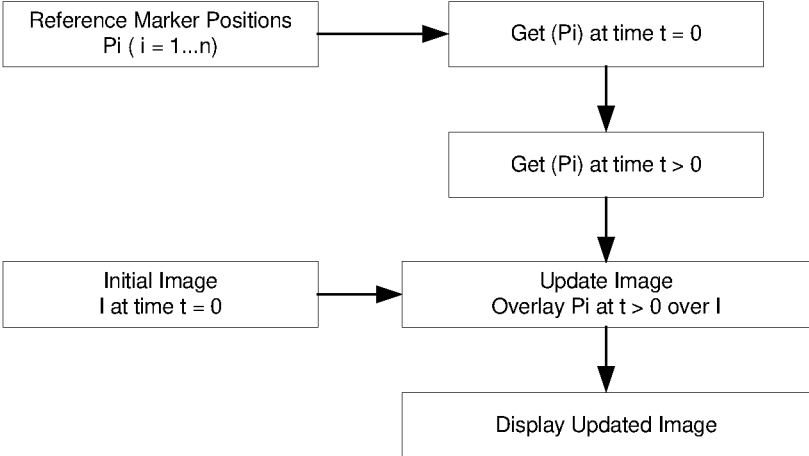
FIG. 8 is a flowchart illustrating another example algorithm in accordance with an example of the present technology.

FIG. 8 is a flowchart illustration an algorithm for updating an image by overlaying movement indicia onto the image. In this example, the initial positions of the reference markers are recorded at time t=0, and then the positions are found again later at time t>0. The initial image/is input as a parameter, and then the initial image is updated by overlaying the positions at time t>0 onto the initial image. The updated image is then displayed.

Figure 9:
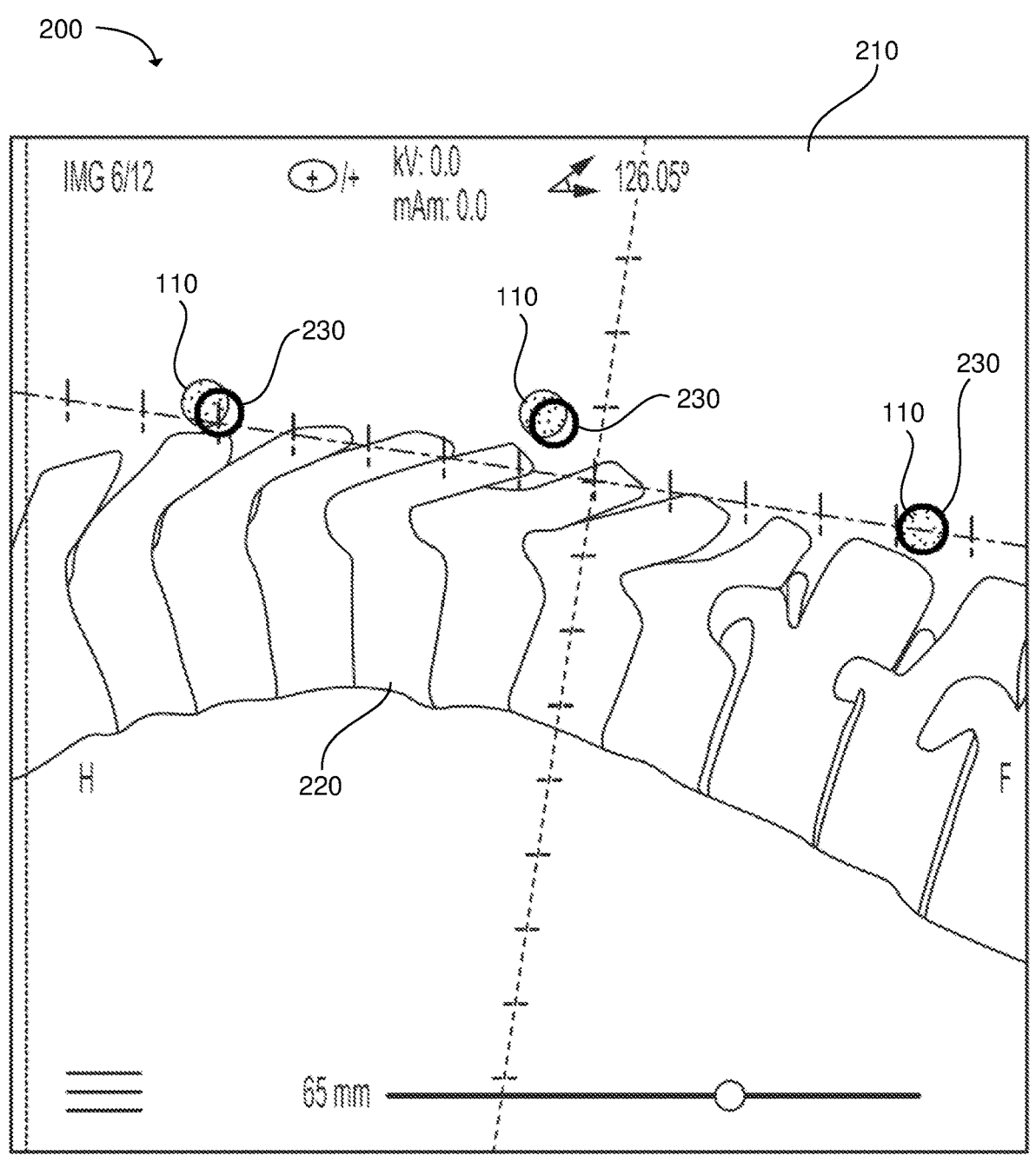
FIG. 9 is an example updated image display in accordance with an example of the present technology.

FIG. 9 shows an example updated image display 200. In this example, a prior image 210 is provided as a scanned image capture using X-ray or CT scanning. The prior image shows a spine 220 and reference markers 110 that were attached the spine before scanning. Specifically, the reference markers included radiopaque reflective spheres that show up as solid circles on the scanned image. The updated image is produced by overlaying movement indicia 230, which in this example are unfilled circles representing the currently tracked positions of the reflective spheres. In this example, a user can view the updated image and deduce that a portion of the spine near the two reference markers on the left side of the image has shifted slightly, as shown by the unfilled circles in a different position than the reflective spheres were in the original image. Similarly, the portion of the spine near the reference marker on the right side of the image likely has not moved as much because the unfilled circle shows the reference marker is still in the same position.

In another option, the processor can be configured to produce the updated image by deforming the prior image via a deformation model. The deformation model can be previously established based on previous patients or other previously available information about the anatomy of interest as previously described. The deformation model may also be updated using information about the current patient, such as by using scanned images of the current patient anatomy to update the model. Movement data of the reference markers can also be input as parameters into the deformation model, resulting in a dynamic map of the patient anatomy. The dynamic map can provide a higher number of degrees of freedom than an individual reference marker, as explained above. In some cases, the dynamic map can provide at least six degrees of freedom, and in many cases, more than six degrees of freedom.

The deformation model can be made more accurate by using similar strategies to those described above to exclude certain reference markers and/or weight the reference markers depending on their confidence level. In one example, model can exclude reference markers that do not behave as expected by the model. For example, the reference markers can be assigned error residuals by the processor. Error residuals above a certain threshold can be excluded or given reduced weight.

Figure 10:
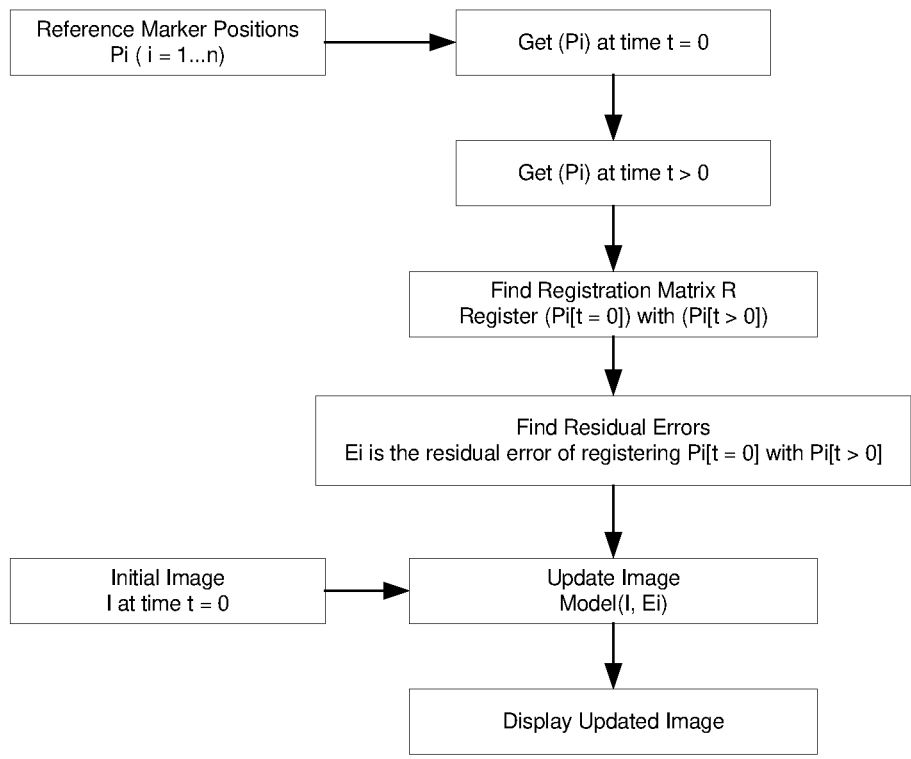
FIG. 10 is a flowchart illustrating another example algorithm in accordance with an example of the present technology.

An example algorithm for producing an updated image through a deformation model is shown in FIG. 10 and consistent with the modeling previously described. In this example, the positions $P_i$ of the reference markers are found at time t=0 and then later at time t>0. A registration matrix R is found by registering $P_i$ at t=0 with $P_i$ at t>0. The residual errors of the registration are found and referred to as $E_i$. The residual errors $E_i$ and the initial image I are parameters input into a deformation model. The model morphs the initial image based on the residual errors to produce an updated image. The updated image is then displayed.

In certain examples, the deformation model can morph the initial image elastically, by stretching the entire image or portions of the image. In some examples, the initial image can be stretched elastically to move the reference markers depicted in the image nearer to the updated positions of the reference markers as tracked by the tracking system.

The model may also utilize image recognition to locate the initial positions of the reference markers in the initial image. Image recognition may also be used to identify rigid tissue, such as bones. Alternatively, the software can be programmed to associated reference markers with a particular tissue. For example, the software can be programmed to expect that any tissue with a reference marker attached is rigid tissue. In other examples, certain reference markers can be attached to rigid tissue and certain other reference markers can be attached to flexible tissue, and the software can be programmed to differentiate between the types of reference markers and thus to know which tissue is flexible or rigid. More specific assignments can also be made, such as assigning a particular reference marker to a particular vertebra.

In certain examples, the model can include a movement model for rigid tissue and a movement model for flexible tissue. For example, the rigid tissue movement model can allow rigid tissue to rotate and shift in space, but not allow the rigid tissue to flex or twist. The flexible tissue movement model can allow the flexible tissue to flex and twist in accordance with previous data on the flexibility of the particular type of tissue. Thus, the model as a whole can simulate the ways in which the patient anatomy is likely to move. When the reference marker position changes, the processor can apply this model and find an arrangement of the rigid and flexible tissue that reduces the residual error between the reference marker location in the image and the reference marker locations tracked by the tracking system, while also being consistent with the expected movement of the rigid tissue and the flexible tissue.

The models described herein can often be based on data from previous patients. However, in some cases, the model can be modified during use using data from the current patient. For example, a second scanned image can be taken and compared with the initial scanned image and with the tracked movement data of the reference markers. The model can then be modified to closer fit the actual movement of the patient anatomy as shown in the second and/or subsequent scanned image.

In further examples, the model can be implemented via regression analysis. As explained above, the regression analysis can include data from previous patients. In some cases, data from a large number of previous patients can be used in a regression analysis to implement the model. Additionally, in some cases data from the current patient can be input into the regression analysis to modify the model for the current patient. Since anatomy varies from patient to patient, it can be more useful to have data from the current patient that to have data from many previous patients. Therefore, in some examples the data from the current patient can be more heavily weighted in the regression analysis when modifying the model.

In other examples, the model can be implemented via a Kalman filter. The Kalman filtering algorithm can be performed using measurements from previous patients and/or the current patient.

Machine learning can also be utilized to implement the deformation model. As in the previous examples, a machine learning model can be prepared using data from previous patients as well as data from the current patient. In some examples, a machine learning model can be trained using learning datasets that include image data and/or tracked movement data of previous patients. The machine learning model can be further trained by adding data from the current patient to the learning dataset. The machine learning model, in one example, can be a convolutional neural network (CNN) trained as a regression network. Other examples of machine learning models can include, but are not limited to, a 3D UNET CNN, dense 3D CNN, or the like.

Accuracy verification of the model can also be performed by using a tracked instrument, as described above. In certain examples, a tracked instrument can be physically touched to one or more of the other reference markers in the system. The tracked positions of the reference markers and the instruments can then be checked to verify the accuracy of the tracking system and the model. In certain examples, one or more of the reference markers can include a feature specifically for verifying accuracy in this way. For example, a reference marker can include a dimple or indentation, and a tracked instrument such as a probe or stylus can be placed with its tip in the dimple. The dimple can provide a precise point to compare the location of the reference marker with the location of the tracked instrument. In another example, the tracked instrument can be touched to anatomical landmarks that are visible in the scanned image, and this can also be used to verify accuracy of the tracking system and the model.

The model can also be programmed to allow additional reference markers to be added midway through a surgery, or for a reference marker to be removed midway through a surgery. This can allow flexibility for removing markers that are in the way of a user or to add additional markers if additional accuracy of tracking is desired.

Although the description above has focused on systems and components of the systems, the present disclosure also describes methods that can be performed using the systems. FIG. 11 is a flowchart illustrating one example method 300 of registering an image of non-rigid anatomy of a patient. This method includes: rigidly attaching two or more reference markers to separate bodies of rigid tissue in a region of a patient to form a marker array, wherein the separate bodies of rigid tissue are connected through flexible tissue 310; using a tracking system to acquire movement data of the two or more reference markers as a function of time and position 320; using a processor, receiving the movement data from the tracking system, wherein an individual reference marker of the two or more reference markers has a first number of degrees of freedom less than 6 (330) and a second reference marker has a second number of degrees of freedom; using the processor, tracking the marker array as a whole with a total number of degrees of freedom greater than the first and second number 340; and using the processor, producing an updated image of the region of the patient to maintain registration to a prior image of the region and the tracked movement of the reference markers via the function 350.

In further examples, methods of registering an image of non-rigid anatomy of a patient can utilize any of the systems and any of the features of the systems described above. Further, renewed images can be acquired periodically during a surgical procedure to create a new image of current actual tissue and reference marker positions. These renewed images can be acquired using a suitable imaging device such as, but not limited to, x-ray computed tomography (CT) imaging system, magnetic resonance imaging (MRI) system, and the like. Of particular interest are CT imaging systems known as C-arm systems which can be readily moved away from a patient in between acquisition of renewed images and do not involve generation of extremely high magnetic fields such as those in MRI systems. Exemplary imaging devices are described in more detail in U.S. Pat. Nos. 10,070,828 and 10,846,860; while image reconstruction techniques such as those describe in these patents can also be particularly effectively used along with additional image reconstruction techniques outlined in U.S. Patent Application Publication No. US-2020-0279411-A1; and U.S. Pat. No. 11,244,481, each of which is incorporated herein by reference.

The renewed images can be acquired ad hoc as determined by a user, and/or may be performed at regular intervals. Such intervals can vary depending on the accuracy needed, the region of tissue, and other factors; however, such intervals can generally range from about 1 to 5 minutes, in some cases, 2 to 10 minutes, and in other cases 5 to 30 minutes. The renewed images become the prior image from which the subsequent updated images are produced using movement data from the tracking system.

EMBODIMENTS

In some examples, the technology can include the following numbered embodiments:

1. A non-rigid anatomy reference system embodiment, comprising:
    two or more reference markers rigidly attachable to separate bodies of rigid tissue in a region of a patient to form a marker array, wherein the separate bodies of rigid tissue are connected through flexible tissue;
    a tracking system configured to acquire movement data of the two or more reference markers as a function of time and position; and
    at least one processor configured to:
        receive the movement data from the tracking system, wherein an individual reference marker of the two or more reference markers has a first number of degrees of freedom less than 6, and a second reference marker has a second number of degrees of freedom, and tracking the marker array as a whole with a total number of degrees of freedom greater than the first and the second number, and
        produce an updated image of the region of the patient to maintain registration to a prior image of the region and the tracked movement of the reference markers via the function of time and position.

2. The system of any of embodiments 1-32, wherein the two or more reference markers include at least one marker which is a 3 degree of freedom marker.

3. The system of any of embodiments 1-32, wherein the two or more reference markers are three or more reference markers and at least one marker which is a 3 degree of freedom marker.

4. The system of embodiment 3, wherein the three of more reference markers include at least three markers which are 3 degree of freedom markers which are also oriented in a non-colinear array when attached.

5. The system of any of embodiments 1-32, wherein a total number of degrees of freedom for the marker array is at least 6.

6. The system of any of embodiments 1-32, wherein the reference markers include at least one independent reference marker and at least one composite reference marker which includes a plurality of reference markers attached to a common support which is attached to rigid tissue of the patient.

7. The system of any of embodiments 1-32, wherein the updated image is an updated visual image.

8. The system of any of embodiments 1-32, wherein the processor is configured to produce the updated image by rigid registration, wherein the prior image is rigidly moved in a direction of movement of at least one of the two or more reference markers.

9. The system of any of embodiments 1-32, wherein the prior image is rigidly moved to align with a new position of the at least one of the two or more reference markers.

10. The system of any of embodiments 1-32, wherein the prior image is rigidly moved by point cloud registration of the two or more reference markers.

11. The system of any of embodiments 1-32, wherein one or more reference markers are excluded from the registration due to registration residuals falling outside of a predetermined confidence range.

12. The system of any of embodiments 1-32, wherein the prior image is rigidly moved by translation, rotation, or a combination thereof.

13. The system of any of embodiments 1-32, wherein the processor is configured to produce the updated image by adjusting a marker image within the movement data to align with the prior image such that corresponding tool markers are also adjusted.

14. The system of any of embodiments 1-32, wherein the processor is configured to produce the updated image by overlaying onto the prior image a movement indicia derived from the movement data of at least one of the two or more reference markers.

15. The system of any of embodiments 1-32, wherein the movement indicia comprises a new position of the at least one of the two or more reference markers.

16. The system of any of embodiments 1-32, wherein the movement indicia comprises a movement vector of the at least one of the two or more reference markers.

17. The system of any of embodiments 1-32, wherein the processor is configured to produce the updated image by deforming the prior image via a deformation model, wherein movement of at least two or more reference markers are an input parameter of the deformation model.

18. The system of any of embodiments 1-32, wherein the deformation model comprises a rigid tissue movement model and a flexible tissue movement model.

19. The system of any of embodiments 1-32, wherein the deformation model includes a machine learning model trained, prior to producing the updated image, to estimate movement of tissue in the region of the patent based on tracked movements of the two or more reference markers, using learning datasets that include image data and tracked movement data of previous patients.

20. The system of any of embodiments 1-32, wherein the learning datasets further include image data and tracked movement data of the patient currently being imaged and tracked.

21. The system of any of embodiments 1-32, wherein the individual reference markers comprise an imageable portion that is light-emitting, radiopaque, visible light reflective, infrared reflective, or a combination thereof.

22. The system of any of embodiments 1-32, wherein the imageable portion is shaped as a sphere, a cube, or a cylinder.

23. The system of any of embodiments 1-32, wherein the individual reference markers further comprise a spacer adjacent to the imageable portion wherein the spacer is configured to space the imageable portion away from the rigid tissue of the patient.

24. The system of any of embodiments 1-32, wherein the spacer spaces the imageable portion from about 5 mm to about 5 cm away from the rigid tissue of the patient.

25. The system of any of embodiments 1-32, wherein the individual reference markers comprise a clip sized and shaped to clip onto the bodies of rigid tissue.

26. The system of any of embodiments 1-32, wherein the clip comprises multiple legs having inwardly oriented teeth configured to grip the bodies of rigid tissue.

27. The system of any of embodiments 1-32, wherein the clip further comprises a spike between the multiple legs configured to press into the bodies of rigid tissue.

28. The system of any of embodiments 1-32, further comprising a surgical instrument comprising an instrument marker, wherein the tracking system is configured to acquire movement data of the instrument marker.

29. The system of any of embodiments 1-32, further comprising an implant comprising an implant marker, wherein the tracking system is configured to acquire movement data of the implant marker.

30. The system of any of embodiments 1-32, wherein the tracking system comprises a visible light camera, an infrared camera, a stereoscopic camera, electromagnetic tracker, or a combination thereof.

31. The system of any of embodiments 1-32, wherein the tracking system is configured to continuously track the two or more reference markers during a surgery.

32. The system of any of embodiments 1-32, wherein the prior image is an X-ray image, a CT scan image, CBCT, TOMO or an MRI image.

33. A method embodiment of registering an image of non-rigid anatomy of a patient, comprising:

rigidly attaching two or more reference markers to separate bodies of rigid tissue in a region of a patient to form a marker array, wherein the separate bodies of rigid tissue are connected through flexible tissue;

using a tracking system to acquire movement data of the two or more reference markers as a function of time and position;

using a processor, receiving the movement data from the tracking system, wherein an individual reference marker of the two or more reference markers has a first number of degrees of freedom less than 6;

using the processor, tracking the marker array as a whole with a second number of degrees of freedom greater than the first number; and using the processor, producing an updated image of the region of the patient to maintain registration to a prior image of the region and the tracked movement of the reference markers via the function.

34. The method of any of embodiments 33-66, wherein the two or more reference markers include at least one marker which is a 3 degree of freedom marker.

35. The method of any of embodiments 33-66, wherein the two or more reference markers are three or more reference markers and at least one marker which is a 3 degree of freedom marker.

36. The method of embodiment 35, wherein the three of more reference markers include at least three markers which are 3 degree of freedom markers which are also oriented in a non-colinear array when attached.

37. The method of any of embodiments 33-66, wherein a total number of degrees of freedom for the marker array is at least 6.

38. The method of any of embodiments 33-66, wherein the reference markers include at least one independent reference marker and at least one composite reference marker which includes a plurality of reference markers attached to a common support which is attached to rigid tissue of the patient.

39. The method of any of embodiments 33-66, wherein the visual image is an updated visual image which is displayed for a user.

40. The method of any of embodiments 33-66, wherein the updated image is produced by rigid registration, wherein the prior image is rigidly moved in a direction of movement of at least one of the two or more reference markers.

41. The method of any of embodiments 33-66, wherein the prior image is rigidly moved to align with a new position of the at least one of the two or more reference markers.

42. The method of any of embodiments 33-66, wherein the prior image is rigidly moved by point cloud registration of the two or more reference markers.

43. The method of any of embodiments 33-66, wherein one or more reference markers are excluded from the registration due to registration residuals falling outside of a predetermined confidence range.

44. The method of any of embodiments 33-66, wherein the prior image is rigidly moved by translation, rotation, or a combination thereof.

45. The method of any of embodiments 33-66, wherein the updated image is produced by adjusting a marker image within the movement data to align with the prior image such that corresponding tool markers are also adjusted.

46. The method of any of embodiments 33-66, wherein the updated image is produced by overlaying onto the prior image a movement indicia derived from the movement data of at least one of the two or more reference markers.

47. The method of any of embodiments 33-66, wherein the movement indicia comprises a new position of the at least one of the two or more reference markers.

48. The method of any of embodiments 33-66, wherein the movement indicia comprises a movement vector of the at least one of the two or more reference markers.

49. The method of any of embodiments 33-66, wherein the updated image is produced by deforming the prior image via a deformation model, wherein movement of at least one of the two or more reference markers is an input parameter of the deformation model.

50. The method of any of embodiments 33-66, wherein the deformation model comprises a rigid tissue movement model and a flexible tissue movement model.

51. The method of any of embodiments 33-66, wherein the deformation model includes a machine learning model trained, prior to producing the updated image, to estimate movement of tissue in the region of the patent based on tracked movements of the two or more reference markers, using learning datasets that include image data and tracked movement data of previous patients.

52. The method of any of embodiments 33-66, wherein the learning datasets further include image data and tracked movement data of the patient currently being imaged and tracked.

53. The method of any of embodiments 33-66, wherein the individual reference markers comprise an imageable portion that is light-emitting, radiopaque, visible light reflective, infrared reflective, or a combination thereof.

54. The method of any of embodiments 33-66, wherein the imageable portion is shaped as a sphere, a cube, or a cylinder.

55. The method of any of embodiments 33-66, wherein the individual reference markers further comprise a spacer adjacent to the imageable portion wherein the spacer is configured to space the imageable portion away from the rigid tissue of the patient.

56. The method of any of embodiments 33-66, wherein the spacer spaces the imageable portion from about 5 mm to about 5 cm away from the rigid tissue of the patient.

57. The method of any of embodiments 33-66, wherein the individual reference markers comprise a clip sized and shaped to clip onto the bodies of rigid tissue.

58. The method of any of embodiments 33-66, wherein the clip comprises multiple legs having inwardly oriented teeth configured to grip the bodies of rigid tissue.

59. The method of any of embodiments 33-66, wherein the clip further comprises a spike between the multiple legs configured to press into the bodies of rigid tissue.

60. The method of any of embodiments 33-66, further comprising introducing a surgical instrument into the region of the patient, wherein the surgical instrument comprises an instrument marker, and using the tracking system to acquire movement data of the instrument marker.

61. The method of any of embodiments 33-66, further comprising introducing an implant into the region of the patient, wherein the implant comprises an implant marker, and using the tracking system to acquire movement data of the implant marker.

62. The method of any of embodiments 33-66, wherein the tracking system comprises a visible light camera, an infrared camera, a stereoscopic camera, electromagnetic tracker, or a combination thereof.

63. The method of any of embodiments 33-66, wherein the tracking system is used to continuously track the two or more reference markers during a surgery.

64. The method of any of embodiments 33-66, wherein the surgery includes surgery on a bone that does not have a reference marker attached.

65. The method of any of embodiments 33-66, wherein the bodies of rigid tissue are vertebrae and wherein the surgery is performed on the spine.

66. The method of any of embodiments 33-66, wherein the prior image is an X-ray image, a CT scan image, or an MRI image.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors, such as CPUs or GPUs, mixed environments and clusters. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions and may even be distributed over several different code segments, among different programs and across several memory devices. Similarly, operational data may be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, a non-transitory machine-readable storage medium, such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

What is claimed is:

1. A non-rigid anatomy reference system, comprising: two or more reference markers rigidly attachable to separate bodies of rigid tissue in a region of a patient to form a marker array, wherein the separate bodies of rigid tissue are connected through flexible tissue; a tracking system configured to acquire movement data of the two or more reference markers as a function of time and position; and at least one processor configured to: receive the movement data from the tracking system, wherein a first reference marker of the two or more reference markers has a first number of degrees of freedom less than 6, and a second reference marker of the two or more reference markers has a second number of degrees of freedom, wherein tracking the marker array with a total number of degrees of freedom is greater than the first number, and produce an updated image of the region of the patient to maintain registration to a prior image of the region and the reference markers via the movement data, wherein the processor is configured to produce the updated image by at least of a rigid registration, wherein the prior image is rigidly moved in a direction of movement of at least one of the two or more reference markers, and deforming the prior image via a deformation model, wherein movement of at least one of the two or more reference markers is an input parameter of the deformation model.

2. The system of claim 1, wherein the two or more reference markers include at least one marker which is a 3 degree of freedom marker.

3. The system of claim 1, wherein the two or more reference markers are three or more reference markers which include at least three markers which are 3 degree of freedom markers which are also oriented in a non-colinear array when attached.

4. The system of claim 1, wherein the total number of degrees of freedom for the marker array is at least 6.

5. The system of claim 1, wherein the two or more reference markers include at least one independent reference marker and at least one composite reference marker which includes a plurality of reference markers attached to a common support which is attached to rigid tissue of the patient.

6. The system of claim 1, wherein the prior image is rigidly moved to align with a new position of the at least one of the two or more reference markers and the prior image is rigidly moved by point cloud registration of the two or more reference markers.

7. The system of claim 6, wherein one or more reference markers are excluded from the registration due to registration residuals falling outside of a predetermined confidence range.

8. The system of claim 1, wherein the prior image is rigidly moved by translation, rotation, or a combination thereof.

9. The system of claim 1, wherein the processor is configured to produce the updated image by adjusting a marker image within the movement data to align with the prior image such that corresponding tool markers are also adjusted.

10. The system of claim 1, wherein the processor is configured to produce the updated image by overlaying onto the prior image a movement indicia derived from the movement data of at least one of the two or more reference markers.

11. The system of claim 1, wherein the deformation model comprises a rigid tissue movement model and a flexible tissue movement model.

12. The system of claim 1, wherein the deformation model includes a machine learning model trained, prior to producing the updated image, to estimate movement of tissue in the region of the patient based on tracked movements of the two or more reference markers, using learning datasets that include image data and tracked movement data of previous patients.

13. The system of claim 12, wherein the learning datasets further include image data and tracked movement data of the patient currently being imaged and tracked.

14. The system of claim 1, wherein the individual reference markers comprise an imageable portion that is light-emitting, radiopaque, visible light reflective, infrared reflective, or a combination thereof.

15. The system of claim 14, wherein the imageable portion is shaped as a sphere, a cube, or a cylinder.

16. The system of claim 14, wherein the individual reference markers further comprise a spacer adjacent to the imageable portion wherein the spacer is configured to space the imageable portion away from the rigid tissue of the patient.

17. The system of claim 1, wherein the individual reference markers comprise a clip sized and shaped to clip onto the bodies of rigid tissue and the clip comprises multiple legs having inwardly oriented teeth configured to grip the bodies of rigid tissue.

18. The system of claim 1, further comprising a surgical instrument comprising an instrument marker, wherein the tracking system is configured to acquire movement data of the instrument marker.

19. The system of claim 1, further comprising an implant comprising an implant marker, wherein the tracking system is configured to acquire movement data of the implant marker.

20. The system of claim 1, wherein the tracking system comprises a visible light camera, an infrared camera, a stereoscopic camera, electromagnetic tracker, or a combination thereof.

21. The system of claim 20, wherein the tracking system is configured to track the two or more reference markers during a surgery.

22. The system of claim 1, further comprising an image device which is configured to acquire a renewed image as an update to replace the prior image, wherein the image device is a CT system or an MRI system, and the prior image is a CT scan image, or an MRI image.

23. A method of registering an image of non-rigid anatomy of a patient, comprising: rigidly attaching two or more reference markers to separate bodies of rigid tissue in a region of a patient to form a marker array, wherein the separate bodies of rigid tissue are connected through flexible tissue; using a tracking system to acquire movement data of the two or more reference markers as a function of time and position; using a processor, receiving the movement data from the tracking system, wherein an first reference marker of the two or more reference markers has a first number of degrees of freedom less than 6, and a second reference marker of the two or more reference markers has a second number of degrees of freedom less than 6; using the processor, wherein tracking the marker array with a total number of degrees of freedom is greater than the first and second number; and using the processor, producing an updated image of the region of the patient to maintain registration to a prior image of the region and the reference markers via the movement data, wherein the updated image is produced by at least one of a rigid registration, wherein the prior image is rigidly moved in a direction of movement of at least one of the two or more reference markers, and deforming the prior image via a deformation model, wherein movement of at least one of the two or more reference markers is an input parameter of the deformation model.

24. The method of claim 23, wherein the two or more reference markers include at least one marker which is a 3 degree of freedom marker and the total number of degrees of freedom for the marker array is at least 6.

25. The method of claim 23, wherein the two or more reference markers are three or more reference markers and the three of more reference markers include at least three markers which are 3 degree of freedom markers which are also oriented in a non-colinear array when attached.

26. The method of claim 23, wherein the prior image is rigidly moved to align with a new position of the at least one of the two or more reference markers, and the prior image is rigidly moved by point cloud registration of the two or more reference markers.

27. The method of claim 23, wherein the updated image is produced by adjusting a marker image within the movement data to align with the prior image such that corresponding tool markers are also adjusted.

28. The method of claim 23, wherein the updated image is produced by overlaying onto the prior image a movement indicia derived from the movement data of at least one of the two or more reference markers.

29. The method of claim 23, wherein the deformation model comprises a rigid tissue movement model and a flexible tissue movement model.

30. The method of claim 23, wherein the deformation model includes a machine learning model trained, prior to producing the updated image, to estimate movement of tissue in the region of the patent based on tracked movements of the two or more reference markers, using learning datasets that include image data and tracked movement data of previous patients.

31. The method of claim 23, wherein the tracking system comprises a visible light camera, an infrared camera, a stereoscopic camera, electromagnetic tracker, or a combination thereof, and the tracking system is used to track the two or more reference markers during a surgery.

32. The method of claim 31, wherein the surgery includes surgery on a bone that does not have a reference marker attached.

33. The method of claim 31, wherein the bodies of rigid tissue are vertebrae and wherein the surgery is performed on a spine.

* * * * *